United States Patent
Hoge et al.

(10) Patent No.: US 9,704,656 B2
(45) Date of Patent: Jul. 11, 2017

(54) LITHIUM SILICATES

(71) Applicant: BASF SE, Ludwigshafen (DE)

(72) Inventors: Berthold Theo Hoge, Bielefeld (DE); Simon Sebastian Steinhauer, Bielefeld (DE); Nikolai Ignatyev, Duisburg (DE); Michael Schulte, Bischofsheim (DE)

(73) Assignee: BASF SE, Ludwigshafen (DE)

( * ) Notice: Subject to any disclaimer, the term of this patent is extended or adjusted under 35 U.S.C. 154(b) by 452 days.

(21) Appl. No.: 14/390,678

(22) PCT Filed: Apr. 2, 2013

(86) PCT No.: PCT/IB2013/052632
§ 371 (c)(1),
(2) Date: Oct. 3, 2014

(87) PCT Pub. No.: WO2013/150448
PCT Pub. Date: Oct. 10, 2013

(65) Prior Publication Data
US 2015/0064551 A1    Mar. 5, 2015

(30) Foreign Application Priority Data

Apr. 5, 2012 (DE) .................. 10 2012 006 897

(51) Int. Cl.
| | |
|---|---|
| *H01B 1/04* | (2006.01) |
| *C07F 7/00* | (2006.01) |
| *H01G 11/62* | (2013.01) |
| *C07F 7/08* | (2006.01) |
| *C07F 1/02* | (2006.01) |
| *C07F 7/12* | (2006.01) |
| *H01M 10/0567* | (2010.01) |
| *H01M 10/0568* | (2010.01) |
| *H01G 11/60* | (2013.01) |
| *H01M 10/0525* | (2010.01) |
| *H01G 11/06* | (2013.01) |

(52) U.S. Cl.
CPC .............. *H01G 11/62* (2013.01); *C07F 1/02* (2013.01); *C07F 7/0803* (2013.01); *C07F 7/12* (2013.01); *H01B 1/04* (2013.01); *H01G 11/60* (2013.01); *H01M 10/0525* (2013.01); *H01M 10/0567* (2013.01); *H01M 10/0568* (2013.01); *H01G 11/06* (2013.01); *H01M 2300/0025* (2013.01); *Y02E 60/13* (2013.01)

(58) Field of Classification Search
CPC ..... H01B 1/00; H01B 1/04; C07F 7/00; C07F 7/08; C07F 7/0803; C07F 7/082; C01B 33/00; C01B 33/10
See application file for complete search history.

(56) References Cited

U.S. PATENT DOCUMENTS

| | | |
|---|---|---|
| 7,973,121 B2 | 7/2011 | Chaussade et al. |
| 2002/0127472 A1 | 9/2002 | Terashima et al. |
| 2009/0099322 A1 | 4/2009 | Chaussade et al. |
| 2011/0291055 A1 | 12/2011 | Kojima et al. |

FOREIGN PATENT DOCUMENTS

| | | |
|---|---|---|
| CN | 101103064 A | 1/2008 |
| CN | 102300811 A | 12/2011 |
| EP | 1 172 877 | 1/2002 |
| EP | 2 394 956 | 12/2011 |
| JP | 63 239780 | 10/1988 |
| JP | 63-239780 A | 10/1988 |
| WO | WO2016146925 A1 * | 9/2016 |

OTHER PUBLICATIONS

Combined Office Action and Search Report issued Dec. 15, 2015 in Chinese Patent Application No. 201380017318.4 (with English translation and English translation of Categories of Cited Documents).
Alexander Kolomeitsev, et al., "Different fluoride anion sources and (trifluoromethyl) trimethylsilane: molecular structure of tris (dimethylamino) sulfonium bis(trifluoromethyl) trimethylsiliconate, the first isolated pentacoordinate silicon species with five Si—C bonds" Chem. Commun.,1999, pp. 1017-1018.
Nicola Maggiarosa, et al., "[ME$_3$Si(CF$_3$)F] and [Me$_3$Si(CF$_3$)$_2$]: Reactive Intermediates in Fluoride-Initiated Trifluoromethylation with Me$_3$SiCF$_3$—An NMR Study", Angew. Chem. Int. Ed., vol. 38, No. 15, pp. 2252-2253, (1999).
International Search Report and Written Opinion of the International Searching Authority Issued Sep. 12, 2013 in PCT/IB13/052632 Filed Apr. 2, 2013.

* cited by examiner

*Primary Examiner* — Mark Kopec
(74) *Attorney, Agent, or Firm* — Oblon, McClelland, Maier & Neustadt, L.L.P.

(57) ABSTRACT

The invention relates to lithium perfluoroalkylfluorosilicates, to their preparation, and to their use as conductive salts in electrochemical cells, more particularly in lithium batteries, lithium ion batteries or lithium ion capacitors, and also to electrolytes or electrochemical cells comprising these lithium perfluoroalkylfluorosilicates.

19 Claims, No Drawings

LITHIUM SILICATES

The invention relates to lithium perfluoroalkylfluorosilicates, to their preparation, and to their use as conductive salts in electrochemical cells, more particularly in lithium batteries, lithium ion batteries or lithium ion capacitors, and also to electrolytes or electrochemical cells comprising these lithium perfluoroalkylfluorosilicates.

A key component of electrochemical devices is the electrolyte. It critically influences the lifetime, reliability, and performance of—for example—a lithium ion battery.

The conductivity of an electrolyte comprising a lithium salt in solution in an organic solvent is determined by the nature of the lithium salt, i.e., by its solubility and the capacity to dissociate into free or solvated cations and anions. The dissociated ions are responsible for charge transfer in electrochemical cells.

In lithium batteries or lithium ion batteries it is common to use lithium hexafluorophosphate as conductive salt, as described for example in W. A. van Schalkwijk and B. Scrosati (Eds.), "Advances in Lithium-Ion Batteries", Kluwer Academic/Plenum Publisher, N.Y., 2002, chapter 5, pages 155-183. A disadvantage is the relatively low stability of this salt toward hydrolysis. A variety of attempts have therefore been made to find a substitute for this salt.

JP 63239780 describes lithium hexafluorosilicate as a possible conductive salt in nonaqueous or polymer electrolytes for lithium batteries.

Lithium hexafluorosilicate possesses the chemical formula $Li_2SiF_6$. Oftentimes the literature uses the chemical formula $LiSiF_6$, but this is chemically not correct—such as in EP 1172877 A1, for example. The solubility of lithium hexafluorosilicate in organic solvents is very low. JP 63239780, for example, prepares a 0.02 M solution of $Li_2SiF_6$ in a mixture of ethylene carbonate and 2-methyltetrahydrofuran in a volume ratio of 1:1.

EP 1172877 A1 describes a secondary battery having a nonaqueous electrolyte, with one of the electrolyte salts being lithium tetrafluoroborate and the other electrolyte salt being—among a number of possibilities—lithium hexafluorosilicate.

The introduction of perfluoroalkyl groups on silicon increases the solubility in organic solvents.

In N. Maggiarosa et al., Angew. Chem. Int. Ed. 1999, 38 (15), 2252-2253, for example, tetramethylammonium salts with the anions $[(CH_3)_3Si(CF_3)F]$ and $[(CH_3)_3Si(CF_3)_2]$ are described, as highly reactive substances, which in the form of intermediate compounds are suitable particularly for the transfer of trifluoromethyl groups.

Tris(dimethylamino)sulfonium bis(trifluoromethyl)trimethylsilicate, for example, can be isolated and is stable at temperatures of up to 00° C. From temperatures of 0 to 5° C., however, the compound undergoes exothermic decomposition, as described in A. Kolomeisev et al., Chem. Commun. 1999, 1017-1018. Such anions are therefore not suitable for new conductive salts.

The object of the invention was therefore to provide suitable conductive salts for electrolytes for use in electrochemical cells that are stable in organic solvents and possess a relatively low molecular weight, thereby facilitating the preparation of 1 M solutions in organic solvents.

Experiments by H. Beckers at Bergische Universitat Gesamthochschule Wuppertal in 1987 were unable to confirm the synthesis of a trifluoromethyl tetrafluorosilicate salt. His dissertation describes, on page 15, the following decomposition:

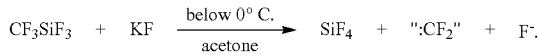

Surprisingly it has been found that perfluoroalkylfluorosilanes can be reacted with lithium fluoride in the presence of an organic solvent, and undergo reaction to form lithium perfluoroalkylfluorosilicates. The object of the invention is therefore achieved by means of lithium perfluoroalkylfluorosilicates in accordance with the present invention.

The invention accordingly first provides the lithium salts of the formula (I) and/or (II)

$$Li[(R_f)_n SiF_{5-n}] \quad (I)$$

$$Li_2[(R_f)_n SiF_{6-n}] \quad (II),$$

where
$R_f$ independently at each occurrence is a straight-chain or branched perfluoroalkyl group having 2 to 12 C atoms and n is an integer from 1 to 4.

A perfluoroalkyl group with 2 to 12 C atoms corresponds to a straight-chain or branched alkyl group having 2 to 12 C atoms wherein all of the H atoms have been replaced by F atoms.

Alkyl groups having 2 to 12 C atoms are, for example, ethyl, isopropyl, propyl, butyl, sec-butyl or tert-butyl, pentyl, 1-, 2-, or 3-methylbutyl, 1,1-, 1,2-, or 2,2-dimethylpropyl, 1-ethylpropyl, n-hexyl, n-heptyl, n-octyl, n-nonyl, n-decyl, n-undecyl or n-dodecyl.

Preferred perfluoroalkyl groups $R_f$ are, in each case independently of one another, a straight-chain or branched perfluoroalkyl group having 2 to 6 C atoms. Particularly preferred perfluoroalkyl groups $R_f$ are, in each case independently of one another, pentafluoroethyl, n-heptafluoropropyl, n-nonafluorobutyl, or n-perfluorohexyl.

In one preferred embodiment of the invention the perfluoroalkyl groups $R_f$ are identical.

The variable n is preferably 1, 2, or 3. The variable n is more preferably 2 or 3. The variable n is very preferably 3.

Preferred compounds of the formula (I) as described above are therefore the salts
lithium tris(pentafluoroethyl)difluorosilicate,
lithium bis(pentafluoroethyl)trifluorosilicate,
lithium tris(n-heptafluoropropyl)difluorosilicate,
lithium bis(n-heptafluoropropyl)trifluorosilicate,
lithium tris(n-nonafluorobutyl)difluorosilicate,
lithium bis(n-nonafluorobutyl)trifluorosilicate,
lithium tris(n-tridecafluorohexyl)difluorosilicate or
lithium bis(n-tridecafluorohexyl)trifluorosilicate.

Preferred compounds of the formula (II) as described above are therefore the salts dilithium tris(pentafluoroethyl)(trifluorosilicate, dilithium bis(pentafluoroethyl)tetrafluorosilicate, dilithium tris(n-heptafluoropropyl)trifluorosilicate, dilithium bis(n-heptafluoropropyl)tetrafluorosilicate, dilithium tris(n-nonafluorobutyl)trifluorosilicate, dilithium bis(n-nonafluorobutyl)tetrafluorosilicate, dilithium tris(n-tridecafluorohexyl)trifluorosilicate, or dilithium bis(n-tridecafluorohexyl)tetrafluorosilicate.

Particularly preferred lithium salts in accordance with the invention are lithium tris(pentafluoroethyl)difluorosilicate and
lithium bis(pentafluoroethyl)trifluorosilicate.

An especially preferred lithium salt in accordance with the invention is lithium tris(pentafluoroethyl)difluorosilicate.

The compounds of the formula (I) as described above can be synthesized by reacting a corresponding silane with lithium fluoride.

The invention accordingly further provides a process for preparing compounds of the formula (I), as described above or described as preferred, wherein a fluoro(perfluoroalkyl) silane of the formula (III),

$(R_f)_n SiF_{4-n}$ (III)

where $R_f$ and n have one of the abovementioned definitions or definitions indicated as being preferred, is reacted with lithium fluoride under dry air or inert gas conditions and in the presence of an organic solvent.

The reaction takes place preferably in a dry atmosphere, as for example under dry air, nitrogen, or argon. With particular preference the reaction is carried out under dry air or a dry nitrogen atmosphere.

The reaction takes place preferably in dried organic solvents. Suitable organic solvents are selected for example from dimethyl carbonate, diethyl carbonate, propylene carbonate, ethylene carbonate, ethyl methyl carbonate, dimethoxyethane, diethyl ether, methyl tert-butyl ether, γ-butyrolactone, tetrahydrofuran, 2-methyltetrahydrofuran, ethyl acetate, or a mixture of said solvents. It is preferred to carry out the reaction in dimethyl carbonate.

Lithium fluoride is introduced in the organic solvent preferably at temperatures from −169° C. to room temperature, more preferably at −169° C., and the compound of the formula (III) is condensed on. The actual reaction then takes place in the course of heating to temperatures between 10° C. and 40° C. The reaction takes place preferably at room temperature (25° C.).

The compounds of the formula (III) are not available commercially, but may be prepared as described in the example section or by methods modified correspondingly to the required silane.

The compound of the formula (III) in which n is 3 and $R_f$ at each occurrence is pentafluoroethyl, i.e., fluorotris(pentafluoroethyl)silane, may be prepared, for example, by reacting bromotris(pentafluoroethyl)silane with $SbF_3$ at room temperature. The detailed reaction conditions and also the preparation of the bromotris(pentafluoroethyl)silane are described in the example section.

The compound of the formula (III) in which n is 2 and $R_f$ at each occurrence is pentafluoroethyl, i.e., difluorobis(pentafluoroethyl)silane, may be obtained, for example, by reaction of methyltris(pentafluoroethyl)silane with fluorine, with subsequent fractional condensation. The detailed reaction conditions are described in the example section.

The compound of the formula (III) in which n is 4 and $R_f$ at each occurrence is pentafluoroethyl, i.e., tetrakis(pentafluoroethyl)silane, may be obtained, for example, by reaction of ethyltris(pentafluoroethyl)silane with fluorine. The detailed reaction conditions are described in the example section.

Alternatively the compounds of the formula (I) and/or (II) may also be prepared by reaction of silicon tetrachloride with the corresponding perfluoroalkyllithium.

The invention accordingly further provides a process for preparing compounds of the formula (I) and/or (II), as described above or described as being preferred, wherein silicon tetrachloride is reacted with perfluoroalkyllithium, where perfluoroalkyl corresponds to a perfluoroalkyl group having 2 to 12 C atoms.

This reaction takes place preferably at temperatures of −78 to −40° C. in an organic solvent. Examples of suitable solvents are dialkyl ethers, in which case the alkyl groups each independently of one another may have 1 to 4 C atoms and may be linear or branched, or mixtures of the dialkyl ethers with hexane. Preferred solvents are diethyl ether or the mixture of diethyl ether and hexane.

Silicon tetrachloride is available commercially. The corresponding perfluoroalkyllithium compounds may be prepared, for example, according to the described methods in P. G. Gassmann, N. J. O'Reilly, *Tetrahedron Lett.* 1985, 26, p. 5243; H. Uno, S.-i. Okada, T. Ono, Y. Shiraishi, H. Suzuki, *J. Org. Chem.* 1992, 57, p. 1504; H. Uno, H. Suzuki, *Synlett*, 1993, p. 91; K. Maruoka, I. Shimada, M. Akakura, H. Yamamoto, *Synlett*, 1994, p. 847.

This alternative reaction generally produces a mixture of compounds of the formula (I) and of the formula (II). Control as to which compound is formed preferentially is accomplished through the proportions of the starting materials used, and through the choice of work-up. Salts of the formula (I) may likewise be isolated as solid or liquid complexes with a solvent, such as with dimethoxyethane, for example.

The invention further provides for the use of at least one compound of the formula (I) and/or of the formula (II), as described above or described as being preferred, as conductive salt in electrochemical cells.

Preferred electrochemical cells are lithium batteries, lithium ion batteries, or lithium capacitors.

The lithium salts of the invention may without further restriction also be used in combination with other conductive salts or additives in the electrochemical cells.

Depending on their concentration in an electrolyte, the lithium salts of the invention may also be additives.

The invention further provides an electrolyte comprising at least one compound of the formula (I) and/or (II) as described above or described as being preferred.

In chemical terms, an electrolyte is any substance which comprises free ions and is therefore electrically conductive. A typical electrolyte is an ionic solution, although melt electrolytes and solid electrolytes are likewise possible.

An electrolyte of the invention or a corresponding electrolyte formulation is therefore an electrically conductive medium, primarily by virtue of the presence of at least one substance which is in the dissolved and/or melted state, i.e., supports electrical conductivity by movement of ions.

The compounds of the invention can be used completely in analogy to alternative lithium compounds which are known for this application, and, when they are used thus, they display extraordinarily high stabilities. Corresponding battery cells exhibit superlative properties in terms of capacity and voltage constancy, and also an unrestricted functionality over an above-averagely high number of charging/discharging cycles.

Where the compounds of the formula (I) and/or formula (II) are used, accordingly, as conductive salt in the electrolytes of the invention, the solutions used are 0.45 to 2 molar, preferably 1 molar, solutions of the lithium conductive salt in an aprotic solvent or solvent mixture.

For the purposes of the present invention, the molarity refers to the concentration at 25° C.

Where the compounds of the formula (I) and/or formula (II) are used as additive in the electrolytes of the invention, the typical concentration is between 0.05 and 10 weight percent, preferably between 0.05% and 5%, based on the total weight of the electrolyte.

Besides the at least one compound of the formula (I) or (II), as described above or described as being preferred, the electrolyte of the invention may comprise an optional further conductive salt, preferably selected from a lithium salt and/or a tetraalkylammonium salt, where each of the alkyl groups independently of the others is an alkyl group having 1 to 4 C atoms.

In one preferred embodiment, when the electrolyte is used in lithium batteries or lithium ion batteries and lithium ion capacitors, the conductive salt is a conductive lithium salt such as $LiPF_6$, $LiBF_4$, $LiN(SO_2F)_2$, $LiN(SO_2CF_3)_2$, $LiN(SO_2C_2F_5)_2$, $LiF_5P(C_2F_5)$, $LiF_5P(C_3F_7)$, $LiF_5P(C_4F_9)$, $LiF_3P(C_2F_5)_3$, $LiF_4P(C_2F_5)_2$, $LiF_3P(C_4F_9)_3$, $LiB(C_2O_4)_2$, or $LiF_2B(C_2O_4)$.

When the electrolyte comprising the at least one compound of the formula (I) or (II) as described above or described as being preferred is used as additive in double-layer capacitors or supercapacitors, the conductive salt is preferably a tetraalkylammonium salt from the group consisting of $[N(C_2H_5)_4]BF_4$, $[N(C_2H_5)_4]PF_6$, $[N(C_2H_5)_3(CH_3)]BF_4$, $[N(C_2H_5)_3(CH_3)]PF_6$, $[N(C_2H_5)_4][N(SO_2CF_3)_2]$, $[N(C_2H_5)_3(CH_3)][N(SO_2CF_3)_2]$, $[N(C_2H_5)_4][PF_3(C_2F_5)_3]$, $[N(C_2H_5)_3(CH_3)][PF_3(C_2F_5)_3]$, $[N(C_2H_5)_4][PF_4(C_2F_5)_2]$, $[N(C_2H_5)_3(CH_3)][PF_4(C_2F_5)_2]$, $[N(C_2H_5)_4][PF_5(C_2F_5)]$, and $[N(C_2H_5)_3(CH_3)][PF_5(C_2F_5)]$.

It is preferred to use 0.45 to 2 molar solutions, more preferably 1 molar solutions, of the conductive lithium salt or of the mixtures of conductive lithium salts in an aprotic solvent or solvent mixture.

The electrolytes of the invention preferably comprise an aprotic solvent or solvent mixture, and also, optionally, further additives. They may be used in combination with other conductive salts and/or adjuvants as part of a polymer electrolyte or phase transfer medium.

The aprotic solvent of the electrolyte preferably consists of organic open-chain or cyclic carbonates, carboxylic esters, nitriles, silanes, or sulfonic esters, or of a mixture thereof.

Preferred open-chain or cyclic carbonates are diethyl carbonate, dimethyl carbonate, ethyl methyl carbonate, ethylene carbonate, or propylene carbonate.

Preferred carboxylic esters are ethyl acetate or methyl propionate.

Preferred nitriles are adiponitrile, valeronitrile, and acetonitrile; acetonitrile is particularly preferred.

The organic solvent is preferably present in the electrolyte at 5 to 90 weight percent, preferably at 40 to 90 weight percent, the weight percentage figure being based on the overall electrolyte.

Other additives may be selected, for example, from the known additives vinylene carbonate, propane sultone, vinyl acetate, biphenyl, cyclohexylbenzene, organic amines, as for example trialkylamines, dialkylphenylamines, or N-silylated amines, such as trimethylsilylimidazole as an example of an N-silylated cyclic amine, or various sulfones, an example being diphenyl sulfone, and the alkyl groups in the aforementioned amines may each independently of one another be a straight-chain or branched alkyl group having 1 to 20 C atoms.

In one preferred embodiment, in addition to the salts of the invention of the formula (I) and/or formula (II), as described above, the electrolyte also comprises the additives of the specified group vinylene carbonate, propane sultone, vinyl acetate, biphenyl, cyclohexylbenzene, organic amines, N-silylated amines, or sulfones, where the alkyl groups in the aforementioned amines may each independently of one another be a straight-chain or branched alkyl group having 1 to 20 C atoms.

Another class of additives which may be present are additives which bring about gelling, for those electrolytes known as gel electrolytes, which are electrolytes which adopt a quasi-solid state. They have structural properties of solid electrolytes, but retain conductive properties like liquid electrolytes.

Gel additives of this kind may be selected from inorganic particulate materials, such as $SiO_2$, $TiO_2$ or $Al_2O_3$, for example. The electrolytes of the invention may comprise such gel additives at 0.01 to 20 weight percent, based on the overall electrolyte, preferably at 1 to 10 weight percent.

When a solvent is present in the electrolyte of the invention there may also be a polymer present, in which case the polymer is polyvinylidene fluoride, polyvinylidene-hexafluoropropene or polyvinylidene hexafluoropropylene-chlorotrifluoroethylene copolymers, Nafion, polyethylene oxide, polymethyl methacrylate, polyacrylonitrile, polypropylene, polystyrene, polybutadiene, polyethylene glycol, polyvinylpyrrolidone, polyaniline, polypyrrole, or polythiophene. These polymers are added to the electrolytes in order to convert liquid electrolytes into quasi-solid or solid electrolytes and so to improve solvent retention, especially on aging.

The electrolytes of the invention are prepared by methods familiar to the skilled person in the field of electrolyte production, generally by dissolving the conductive salt in the corresponding solvent mixture and adding other adjuvants.

The invention further provides an electrochemical cell comprising at least one compound of the formula (I) and/or formula (II) as described above or described as being preferred.

The electrochemical cell is preferably a lithium battery, a lithium ion battery, or a lithium ion capacitor.

A lithium battery is a battery in which a lithium metal electrode is used as negative electrode.

As its negative electrode a lithium ion battery uses materials into which lithium can be intercalated or removed reversibly. Examples of such materials are graphite, silicon or silicon-carbon composites, tin oxides, or lithium titanium oxides.

The general construction of such electrochemical cells is known and is familiar to the skilled person in this field—for batteries, for example, in Linden's Handbook of Batteries (ISBN 978-0-07-162421-3).

The anode consists, for example, of carbon/graphite, the cathode of a lithium metal oxide or lithium (iron) phosphate, and the separator of polypropylene/polyethylene or ceramic film.

Even without further observations, it is assumed that a skilled person will be able to utilize the above description to its widest extent. Consequently, the preferred embodiments and examples are to be interpreted merely as a descriptive disclosure which in no way has any limiting effect at all.

The compounds obtained are characterized by elemental analysis and NMR spectroscopy.

NMR spectra are recorded using the Avance 250 and Avance II 300 spectrometers from Bruker, Karlsruhe, Germany. Acetone-$D_6$ is used in a capillary as lock substance. Referencing is accomplished using an external reference: TMS for $^1H$ and $^{13}C$ spectra; $CCl_3F$—for $^{19}F$ spectra; and 85% $H_3PO_4$—for $^{31}P$ spectra.

EXAMPLE 1

Preparation of Diethylaminotris(Pentafluoroethyl)Silane

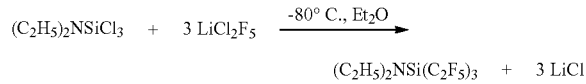

$(C_2H_5)_2NSiCl_3 + 3\ LiCl_2F_5 \xrightarrow{-80°\ C.,\ Et_2O} (C_2H_5)_2NSi(C_2F_5)_3 + 3\ LiCl$ 100 ml of diethyl ether and 34 ml of 1.6 M (54 mmol) n-butyllithium in hexane are introduced in a Schlenk flask and degassed at −85° C. After 56 mmol of pentafluoroethane have been condensed on, the solution is stirred at −80° C. for 45 minutes. Then, slowly, 3.1 g (15 mmol) of $Et_2NSiCl_3$ are added dropwise. The reaction mixture is warmed slowly from −80° C. to room temperature (RT) in a refrigeration bath, with the possibility of pressure compensation. The resulting precipitate is removed by filtration on a double-ended frit. The solvents are removed on a rotary evaporator. The slightly yellowish residue is subjected to fractional distillation. At a pressure of 66 mbar and an overhead temperature of 98° C., $(C_2F_5)_3SiNEt_2$ is obtained as a clear, colorless liquid. Yield: 5.7 g (12.4 mmol) 82% (based on $SiCl_3NEt_2$).

NMR Spectroscopic Data of $(C_2F_5)_3SiNEt_2$ in $CDCl_3$, RT.

| Nucleus | δ/ppm | Splitting | J/Hz | Assignment |
|---|---|---|---|---|
| $^{19}F$ | −81.8 | s | — | $[Si(CF_2CF_3)_3NEt_2]$ |
|  | −121.5 | s | — | $[Si(CF_2CF_3)_3NEt_2]$ |
| 1H | 3.1 | q | $^3J_{HH} = 7.0$ | $[Si(CF_2CF_3)_3N(CH_2CH_3)_2]$ |
|  | 1.1 | t | $^3J_{HH} = 7.0$ | $[Si(CF_2CF_3)_3N(CH_2CH_3)_2]$ |
| $^{29}Si\{^{19}F\}$ | −41.6 | quin | $^3J_{SiH} = 4.1$ | $[Si(CF_2CF_3)_3NEt_2]$ |
| $^{29}Si\{1H\}$ | −41.6 | sept | $^3J_{SiF} = 36$ | $[Si(CF_2CF_3)_3NEt_2]$ |
| $^{13}C\{^{19}F\}$ | 119.5 | s | — | $[Si(CF_2CF_3)_3NEt_2]$ |
|  | 116.1 | s | — | $[Si(CF_2CF_3)_3NEt_2]$ |
| $^{13}C\{^1H\}$ | 39.3 | s | — | $[Si(CF_2CF_3)_3N(CH_2CH_3)_2]$ |
|  | 12.5 | s | — | $[Si(CF_2CF_3)_3N(CH_2CH_3)_2]$ |

EXAMPLE 2

Preparation of Tetrakis(Pentafluoroethyl)Silane

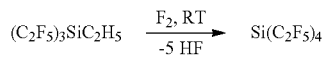

$(C_2F_5)_3SiC_2H_5 \xrightarrow[-5\ HF]{F_2,\ RT} Si(C_2F_5)_4$ 124 mg of $(C_2F_5)_3SiC_2H_5$ (0.3 mmol) are condensed in a FEP reactor and admixed at −120° C. with 3 mmol of $F_2$ (5% in He). The gaseous reaction mixture is circulated at room temperature for 2 hours by means of a pump in a stainless steel unit (316) passivated with $F_2$. Then all of the condensable constituents are frozen out at −196° C. At −78° C., all of the volatile constituents are separated off, and the liquid residue, contaminated with a little HF, is analyzed in pentane by NMR spectroscopy. It is found to be a product mixture consisting of $Si(C_2F_5)_4$ and $(C_2F_5)_3SiF$ in a 10:1 ratio.

$^{29}Si$ NMR Spectroscopy Data for the Product Mixture (Solvent: Pentane)

| δ/ppm | Multiplicity | J/Hz | Assignment |
|---|---|---|---|
| −35.8 | nonet | $^2J(SiF) = 39$ | $Si(C_2F_5)_4$ |
| −60.7 | m | — | $(C_2F_5)_3SiF$ |

$^{19}F$ NMR Spectroscopic Data of the Product Mixture Solvent Pentane)

| δ/ppm | Assignment | Integral |
|---|---|---|
| −82.9 | $Si(CF_2CF_3)_4$ | 12 |
| −84.2 | $(CF_3CF_2)_3SiF$ | 0.7 |
| −117.7 | $Si(CF_2CF_3)_4$ | 8 |
| −132.1 | $(CF_3CF_2)_3SiF$ | 0.5 |

EXAMPLE 3

Preparation of Bromotris(Pentafluoroethyl)Silane $Et_2NSi(C_2F_5)_3 + 2HBr \rightarrow (C_2F_5)_3SiBr + [H_2NEt_2]Br$ Diethylaminotris(pentafluoroethyl)silane (22.9 g, 50 mmol) is introduced in a Schlenk flask, and hydrogen bromide (140 mmol) is condensed on. The contents of the flask are warmed to room temperature. The volatile constituents are transferred by condensation into a cold trap with a temperature of −196° C. Excess HBr is removed by fractional condensation using a cold trap cooled to −78° C. The tris(pentafluoroethyl)bromosilane (0.688 g, 1.48 mmol, 89%) is obtained as a colorless liquid. Yield: 22.7 g (12.4 mmol) 98% (based on $Et_2NSi(C_2F_5)_3$).

NMR Spectroscopic Data of $Si(C_2F_5)_3Br$ in Pentane, RT

| Nucleus | δ/ppm | Splitting | J/Hz | Assignment |
|---|---|---|---|---|
| $^{19}F$ | −80.8 | s | — | $[Si(CF_2CF_3)_3Br]$ |
|  | −121.1 | s | $^1J_{CF} = 277$ | $[Si(CF_2CF_3)_3Br]$ |
| $^{29}Si$ | −22.7 | sept | $^2J_{SiF} = 43$ | $[Si(CF_2CF_3)_3Br]$ |
| $^{13}C\{^{19}F\}$ | 118.9 | s | — | $[Si(CF_2CF_3)_3Br]$ |
|  | 114.2 | s | $^1J_{SiC} = 79$ | $[Si(CF_2CF_3)_3Br]$ |

EXAMPLE 4

Preparation of Fluorotris(Pentafluoroethyl)Silane

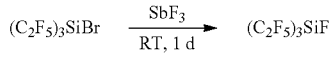

$(C_2F_5)_3SiBr \xrightarrow[RT,\ 1\ d]{SbF_3} (C_2F_5)_3SiF$

In a 100 ml flask with a Young tap, 0.9 g (5 mmol) of $SbF_3$ is introduced and 1.6 g (3.5 mmol) of $(C_2F_5)_3SiBr$ are condensed on. After a day of stirring, $(C_2F_5)_3SiF$ can be condensed off as a clear colorless liquid. Yield: 1.2 g (3.0 mmol) 86% (based on $(C_2F_5)_3SiBr$).

NMR Spectroscopic Data of $(C_2F_5)_3SiF$ as Pure Substance, RT.

| Nucleus | δ/ppm | Splitting | J/Hz | Assignment |
|---|---|---|---|---|
| $^{19}F$ | −83.9 | m | — | $[Si(CF_2CF_3)_3F]$ |
|  | −127.3 | m | — | $[Si(CF_2CF_3)_3F]$ |
|  | −181.2 | m | $^1J_{Si} = 345.0$ | $[Si(CF_2CF_3)_3F]$ |

-continued

| Nucleus | δ/ppm | Splitting | J/Hz | Assignment |
|---|---|---|---|---|
| $^{13}C\{^{19}F\}$ | 118.2 | s | — | [Si(CF$_2$CF$_3$)$_3$H] |
| DEPT | 113.5 | d | — | [Si(CF$_2$CF$_3$)$_3$F] |
| $^{29}$Si IG | −33.0 | d sept | $^1J_{SiF}$ = 345.0 | [Si(CF$_2$CF$_3$)$_3$F] |
| | | | $^2J_{SiF}$ = 43.7 | |

EXAMPLE 5

Preparation of Methyltris(Pentafluoroethyl)Silane

$$CH_3SiCl_3 + 3\ LiC_2F_5 \xrightarrow{-80°\ C.,\ Et_2O} CH_3Si(C_2F_5)_3 + 3\ LiCl$$

150 ml of diethyl ether and 52 ml of 2 M (104 mmol) n-butyllithium in pentane are introduced in a Schlenk flask and degassed at −85° C. After 120 mmol of pentafluoroethane have been condensed on, the solution is stirred at −80° C. for 45 minutes. Then, slowly, 5 g (33 mmol) of CH$_3$SiCl$_3$ are added dropwise. The reaction mixture is warmed slowly from −80° C. to RT in a refrigeration bath, with the possibility of pressure compensation. The resulting precipitate is isolated by filtration on a double-ended frit. The solvents are distilled off using a Claisen bridge. The slightly yellowish residue is subjected to fractional distillation. Under atmospheric pressure and at an overhead temperature of 56° C., CH$_3$Si(C$_2$F$_5$)$_3$ is obtained as a clear colorless liquid. Yield: 7.6 g (19 mmol) 57% (based on CH$_3$SiCl$_3$).

NMR Spectroscopic Data of Si(C$_2$F$_5$)$_3$CH$_3$ in CDCl$_3$, RT

| Nucleus | δ/ppm | Splitting | J/Hz | Assignment |
|---|---|---|---|---|
| $^{19}$F | −81.5 | s | — | [Si(CF$_2$CF$_3$)$_3$Me] |
| | −122.8 | s | — | [Si(CF$_2$CF$_3$)$_3$Me] |
| 1H | 0.93 | s | $^2J_{SiF}$ = 35 | [Si(CF$_2$CF$_3$)$_3$Me] |
| $^{29}$Si | −9.9 | sept. q | $^2J_{SiH}$ = 7.7 | [Si(CF$_2$CF$_3$)$_3$Me] |
| $^{13}C\{^{19}F\}$ | 118.8 | s | $^2J_{SiC}$ = 8 | [Si(CF$_2$CF$_3$)$_3$Me] |
| | 115.6 | s | $^3J_{CH}$ = 2 | [Si(CF$_2$CF$_3$)$_3$Me] |
| $^{13}C\{^1H\}$ | 10.8 | s | — | [Si(CF$_2$CF$_3$)$_3$Me] |

EXAMPLE 6

Preparation of Fluorotris(Pentafluoroethyl)Silane

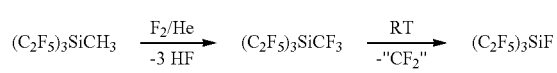

$$(C_2F_5)_3SiCH_3 \xrightarrow[-3\ HF]{F_2/He} (C_2F_5)_3SiCF_3 \xrightarrow[-"CF_2"]{RT} (C_2F_5)_3SiF$$

(C$_2$F$_5$)$_3$SiCH$_3$ (340 mg, 0.85 mmol) is condensed into a reaction vessel, admixed four times with 1 mmol of F$_2$ each time, and stirred at room temperature for an hour. Then all of the volatile substances are condensed into a cold trap. The respective gas space is withdrawn at −75° C. and discarded. The residue (0.306 g) is analyzed by NMR spectroscopy.

After 14 hours at room temperature, 90% of the original amount of (C$_2$F$_5$)$_3$SiCF$_3$ has been converted, with elimination of C$_2$F$_4$ and C$_3$F$_6$, into (C$_2$F$_5$)$_3$SiF.

$^{29}$Si NMR Spectroscopic Data of the Reaction Mixture (without Solvent)

| δ/ppm | Multiplicity | J/Hz | Assignment |
|---|---|---|---|
| −34.0 | m | $^1$J(SiF) = 345 | (C$_2$F$_5$)$_3$SiF |
| −40.1 | m | — | (C$_2$F$_5$)$_3$SiCF$_3$ |
| −60.5 | m | — | (C$_2$F$_5$)$_2$SiF$_2$ |

$^{19}$F NMR Spectroscopic Data of the Reaction Mixture (without Solvent)

| δ/ppm | Multiplicity | J/Hz | Assignment | Integral |
|---|---|---|---|---|
| −56.2 | m | $^2$J(SiF) = 48 | (C$_2$F$_5$)$_3$SiCF$_3$ | 3 |
| −84.6 | m | — | (CF$_3$CF$_2$)$_3$SiCF$_3$ | 9 |
| −84.8 | m | — | (CF$_3$CF$_2$)$_3$SiF | 9 |
| −85.8 | m | — | (CF$_3$CF$_2$)$_2$SiF$_2$ | 0.7 |
| −120.6 | m | $^2$J(SiF) = 37 | (CF$_3$CF$_2$)$_3$SiCF$_3$ | 6 |
| −128.3 | m | $^2$J(SiF) = 40 | (CF$_3$CF$_2$)$_3$SiF | 8 |
| −133.5 | m | $^2$J(SiF) = 43 | (CF$_3$CF$_2$)$_2$SiF$_2$ | 0.6 |
| −151.6 | m | $^1$J(SiF) = 325 | (C$_2$F$_5$)$_2$SiF$_2$ | 0.2 |
| −182.2 | m | $^1$J(SiF) = 342 | (C$_2$F$_5$)$_3$SiF | 1 |

EXAMPLE 7

Preparation of Lithium Tris(Pentafluoroethyl)Difluorosilicate(-1), Li[(C$_2$F$_5$)$_3$SiF$_2$]

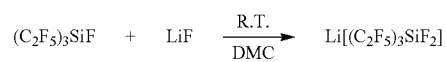

$$(C_2F_5)_3SiF + LiF \xrightarrow[DMC]{R.T.} Li[(C_2F_5)_3SiF_2]$$

In a Schlenk flask under an N$_2$ atmosphere, 624.5 mg (24 mmol) of LiF are introduced in 24 ml (25.77 g) of dimethyl carbonate (DMC), (CH$_3$O)$_2$CO (dried over molecular sieve and freshly distilled) is introduced, and 9.723 g (24 mmol) of (C$_2$F$_5$)$_3$SiF are condensed on at −196° C. On warming to RT, with stirring, the LiF goes into solution. The yield of Li[(C$_2$F$_5$)$_3$SiF$_2$] is quantitative.

NMR Spectroscopic Data of Li[Si(C$_2$F$_5$)$_3$F$_2$] in (CH$_3$O)$_2$CO Using Acetone-D$_6$ as External Lock Substance, RT.

| Nucleus | δ/ppm | Splitting | J/Hz | Assignment |
|---|---|---|---|---|
| $^{19}$F | −84.4 | t | $^4J_{FF}$ = 8 Hz | [Si(CF$_2$CF$_3$)$_3$F$_2$]$^-$ |
| | −128.0 | t | $^3J_{FF}$ = 8 Hz | [Si(CF$_2$CF$_3$)$_3$F$_2$]$^-$ |
| | −107.9 | m | | [Si(CF$_2$CF$_3$)$_3$F$_2$]$^-$ |

The conductivity for a solution of 10.3 g (24 mmol) of Li[(C$_2$F$_5$)$_3$SiF$_2$] in 24 ml of dimethyl carbonate is as follows:

| Temperature, ° C. | Conductivity, mS/cm$^2$ |
|---|---|
| −20 | 1.39 |
| −10 | 3.43 |
| 0 | 6.62 |
| 20 | 9.51 |
| 40 | 12.42 |
| 60 | 15.80 |
| 80 | 19.19 |

EXAMPLE 8

Preparation of Dilithium Tris(Pentafluoroethyl)Trifluorosilicate(-2), $Li_2[Si(C_2F_5)_3F_3]$

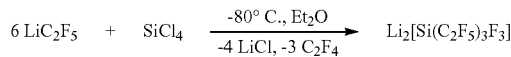

A mixture of 50 ml of diethyl ether and 10 ml of 1.6 M (16 mmol) n-butyllithium in hexane is degassed at −92° C. and 20 mmol of pentafluoroethane are condensed on. The colorless solution is subsequently stirred at −90° C. for 15 minutes and 0.32 g (1.9 mmol) of $SiCl_4$ are condensed on. The reaction mixture is warmed slowly from −80° C. to RT in a refrigeration bath, and the product is characterized by NMR spectroscopy.

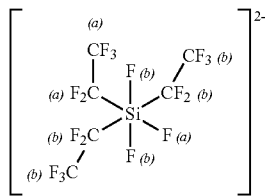

NMR Spectroscopic Data for $Li_2[Si(C_2F_5)_3F_3]$ in $Et_2O$, RT.

| Nucleus | δ/ppm | J/Hz | Assignment |
|---|---|---|---|
| $^{29}Si\{^{19}F\}$ | −177.8 | | $[Si(CF_2CF_3)_3F_3]^{2-}$ |
| $^{19}F$ | −82.1 | | $CF_3(b)$ |
| | −82.8 | | $CF_3(a)$ |
| | −111.8 | $^1J_{SiF} = 205$ | F(a) |
| | −124.4 | | $CF_2(b)$ |
| | −124.8 | | $CF_2(a)$ |
| | −144.2 | $^1J_{SiF} = 235$ | F(b) |

The invention claimed is:

1. A compound of formula (I)

$$Li[(R_f)_nSiF_{5-n}] \quad (I)$$

wherein $R_f$ independently at each occurrence is a straight-chain or branched perfluoroalkyl group having 2 to 12 C atoms and n is an integer of from 1 to 4.

2. The compound according to claim 1, wherein the variable n is 1, 2, or 3.

3. The compound according to claim 1, wherein the variable n is 2 or 3.

4. The compound according to claim 1, wherein the perfluoroalkyl group $R_f$ is identical at each occurrence.

5. A process for preparing a compound of formula (I) according to claim 1, comprising reacting a fluoro(perfluoroalkyl)silane of formula (III)

$$(R_f)_nSiF_{4-n} \quad (III)$$

where wherein $R_f$ and n have the definition stated in claim 1 with lithium fluoride under dry air or inert gas conditions and in the presence of an organic solvent.

6. A process for preparing a compound of formula (I) according to claim 1, comprising reacting silicon tetrachloride with perfluoroalkyllithium, where perfluoroalkyl corresponds to a perfluoroalkyl group having 2 to 12 C atoms.

7. A process comprising employing a compound according to claim 1 to an electrochemical cell as a conductive salt.

8. The process according to claim 7, wherein the electrochemical cell is a lithium battery or a lithium ion battery or a lithium ion capacitor.

9. An electrolyte comprising at least one a compound according to claim 1.

10. An electrochemical cell comprising a compound according to claim 1.

11. A compound of formula (II)

$$Li_2[(R_f)_nSiF_{6-n}] \quad (II)$$

wherein $R_f$ independently at each occurrence is a straight-chain or branched perfluoroalkyl group having 2 to 12 C atoms and n is an integer of from 1 to 4.

12. The compound according to claim 11, wherein the variable n is 1, 2, or 3.

13. The compound according to claim 11, wherein the variable n is 2 or 3.

14. The compound according to claim 11, wherein the perfluoroalkyl group $R_f$ is identical at each occurrence.

15. A process for preparing a compound of formula (II) according to claim 11, comprising reacting silicon tetrachloride with perfluoroalkyllithium, where perfluoroalkyl corresponds to a perfluoroalkyl group having 2 to 12 C atoms.

16. A mixture comprising a compound of formula (I) and a compound of formula (II)

$$Li[(R_f)_nSiF_{5-n}] \quad (I)$$

$$Li_2[(R_f)_nSiF_{6-n}] \quad (II)$$

wherein $R_f$ independently at each occurrence is a straight-chain or branched perfluoroalkyl group having 2 to 12 C atoms and n is an integer of from 1 to 4.

17. The mixture according to claim 16, wherein the variable n is 1, 2, or 3.

18. The mixture according to claim 16, wherein the variable n is 2 or 3.

19. The mixture according to claim 16, wherein the perfluoroalkyl group $R_f$ is identical at each occurrence.

* * * * *